US010634660B2

(12) United States Patent
Brun et al.

(10) Patent No.: US 10,634,660 B2
(45) Date of Patent: Apr. 28, 2020

(54) ELECTRICAL CHARACTERISTIC MEASUREMENT DEVICE, ELECTRICAL CHARACTERISTIC MEASUREMENT METHOD, AND BLOOD CONDITION ANALYSIS SYSTEM

(71) Applicant: SONY CORPORATION, Tokyo (JP)

(72) Inventors: Marcaurele Brun, Tokyo (JP); Isao Hidaka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 66 days.

(21) Appl. No.: 15/560,172

(22) PCT Filed: Feb. 29, 2016

(86) PCT No.: PCT/JP2016/055974
§ 371 (c)(1),
(2) Date: Sep. 21, 2017

(87) PCT Pub. No.: WO2016/158139
PCT Pub. Date: Oct. 6, 2016

(65) Prior Publication Data
US 2018/0080920 A1   Mar. 22, 2018

(30) Foreign Application Priority Data
Mar. 31, 2015   (JP) .................................. 2015-074030

(51) Int. Cl.
*G01N 33/49*   (2006.01)
*G01N 21/59*   (2006.01)
(Continued)

(52) U.S. Cl.
CPC ............. *G01N 33/49* (2013.01); *G01N 21/59* (2013.01); *G01N 27/06* (2013.01);
(Continued)

(58) Field of Classification Search
CPC ..... G01N 33/49; G01N 33/4905; G01N 27/06
See application file for complete search history.

(56) References Cited

U.S. PATENT DOCUMENTS

| 6,228,652 B1 * | 5/2001 | Rodriguez | ............. G01N 15/14 356/335 |
| 7,729,866 B2 * | 6/2010 | Sugiyama | .......... G01N 27/3271 204/403.01 |

(Continued)

FOREIGN PATENT DOCUMENTS

| CN | 105008907 A | 10/2015 |
| EP | 2975388 A1 | 1/2016 |

(Continued)

OTHER PUBLICATIONS

International Search Report and Written Opinion of PCT Application No. PCT/JP2016/055974, dated Apr. 26, 2016, 09 pages of ISRWO.

*Primary Examiner* — Tung X Nguyen
*Assistant Examiner* — Dominic E Hawkins
(74) *Attorney, Agent, or Firm* — Chip Law Group

(57) ABSTRACT

A technology of measuring an electrical characteristic of a blood sample is provided that allows easy introduction, into an existing blood test system, a technique of obtaining information on a blood sample from an electrical characteristic of the blood sample. The technology provides a device for measuring an electrical characteristic of a blood sample, the device including: a mixing unit configured to mix a blood cell component and a plasma component on the basis of the composition ratio between the blood cell component and the plasma component in a blood sample; and a blood sample measurement unit configured to measure an electrical characteristic of a blood sample obtained by mixing by the mixing unit.

11 Claims, 7 Drawing Sheets

(51) Int. Cl.
  *G01N 27/06* (2006.01)
  *G01N 33/86* (2006.01)
  *G01N 13/00* (2006.01)
(52) U.S. Cl.
  CPC ......... *G01N 33/4905* (2013.01); *G01N 13/00* (2013.01); *G01N 33/491* (2013.01); *G01N 33/86* (2013.01)

(56) References Cited

U.S. PATENT DOCUMENTS

| | | | | |
|---|---|---|---|---|
| 2001/0055812 A1* | 12/2001 | Mian | ................... | B01F 13/0059 436/45 |
| 2003/0066807 A1* | 4/2003 | Suzuki | ................ | A61M 1/0209 210/782 |
| 2004/0069708 A1* | 4/2004 | Laurell | ............... | A61M 1/3479 210/646 |
| 2008/0187951 A1* | 8/2008 | Nagai | ................... | G01N 15/12 435/29 |
| 2010/0248247 A1* | 9/2010 | Kataoka | ................. | G01N 33/49 435/6.1 |
| 2011/0053212 A1* | 3/2011 | Matsumoto | ........ | G01N 33/5094 435/34 |
| 2012/0035450 A1* | 2/2012 | Hayashi | ............. | G01N 33/4905 600/369 |
| 2012/0048732 A1* | 3/2012 | Hayashi | ............. | G01N 33/4905 204/403.02 |
| 2013/0171681 A1* | 7/2013 | Shibata | .................... | G01N 1/10 435/29 |
| 2013/0289650 A1* | 10/2013 | Karlsson | ............ | A61N 1/36117 607/44 |
| 2014/0065715 A1* | 3/2014 | Shin | ........................ | G01N 33/86 436/69 |
| 2015/0025341 A1* | 1/2015 | Sakota | ................... | G01N 21/05 600/322 |
| 2015/0148212 A1* | 5/2015 | Chiyoda | ............ | G01N 33/5002 494/37 |
| 2016/0001834 A1 | 1/2016 | Ramraika et al. | | |
| 2016/0077037 A1* | 3/2016 | Cha | ..................... | G01N 27/3274 205/777.5 |

FOREIGN PATENT DOCUMENTS

| | | |
|---|---|---|
| JP | 58-137758 A | 8/1983 |
| JP | 09-89907 A | 4/1997 |
| JP | 09-089907 A | 4/1997 |
| JP | 2002-333361 A | 11/2002 |
| JP | 2008-279195 A | 11/2008 |
| JP | 2010-181400 A | 8/2010 |
| WO | 2014/141844 A1 | 9/2014 |

\* cited by examiner

ELECTRICAL CHARACTERISTIC MEASUREMENT DEVICE, ELECTRICAL CHARACTERISTIC MEASUREMENT METHOD, AND BLOOD CONDITION ANALYSIS SYSTEM

CROSS REFERENCE TO RELATED APPLICATIONS

This application is a U.S. National Phase of International Patent Application No. PCT/JP2016/055974 filed on Feb. 29, 2016, which claims priority benefit of Japanese Patent Application No. JP 2015-074030 filed in the Japan Patent Office on Mar. 31, 2015. Each of the above-referenced applications is hereby incorporated herein by reference in its entirety.

TECHNICAL FIELD

The present technology relates to an electrical characteristic measurement device. More specifically, the present technology relates to a device for measuring an electrical characteristic of a blood sample containing a blood cell component and a plasma component, an electrical characteristic measurement method, a blood condition analysis system, and a program for causing a computer to execute the method.

BACKGROUND ART

Methods for clinically analyzing the condition of blood include, for example, blood coagulation tests and blood ammonia tests. General known blood coagulation tests include, for example, prothrombin time (PT) tests and activated partial thromboplastin time (APTT) tests. These methods include analyzing proteins that are involved in coagulation reactions and contained in plasma obtained by centrifuging a blood sample.

Also general blood ammonia tests include analyzing ammonium ions in plasma obtained by centrifuging a blood sample similarly to the blood coagulation tests.

In methods for clinically analyzing the condition of blood, plasma obtained by centrifuging a blood sample as mentioned above is subjected to various tests in which a certain substance in the plasma is used as an index.

Therefore, the step of promptly centrifuging blood samples taken from, for example, patients is adopted for blood test systems introduced in medical institutions such as inspection institutions and hospitals where blood condition analysis methods are clinically performed.

On the other hand, now, techniques for observing the condition of blood samples on the basis of electrical characteristics of the blood samples are being developed. For example, Patent Document 1 discloses a technique of obtaining information on blood coagulation from an electrical characteristic, such as permittivity, of a blood sample, in which the electrical characteristic is used as an index. Patent Document 1 also describes a blood coagulation system analysis device including: a pair of electrodes; means for applying an alternating voltage to the pair of electrodes at predetermined time intervals; means for measuring the permittivity of blood disposed between the pair of electrodes; and means for analyzing the level of activity of the blood coagulation system using the permittivity of blood measured at the predetermined time intervals after the action of an anticoagulant on the blood is stopped.

In this technique, a whole-blood-state blood sample containing all blood components, which is not separated into blood components such as a plasma component and a blood cell component, is used for obtaining information on the blood sample, such as information on blood coagulation, from the permittivity of the blood sample.

CITATION LIST

Patent Document

Patent Document 1: Japanese Patent Application Laid-Open No. 2010-181400

SUMMARY OF THE INVENTION

Problems to be Solved by the Invention

As mentioned above, the use of a whole-blood-state blood sample is a precondition for the technique of obtaining information on a blood sample from an electrical characteristic of the blood sample.

On the other hand, as mentioned above, blood test systems introduced in medical institutions and so on are based on the premise that the plasma component is obtained by subjecting blood samples to centrifugation.

Therefore, the technique of obtaining information on a blood sample from an electrical characteristic of the blood sample cannot be performed on a blood sample having undergone the separation step. On the other hand, in a case where an electrical characteristic of a blood sample is measured before the blood sample is subjected to the separation step, it is necessary to open the lid of a vessel, such as a blood-collecting vessel, containing a whole-blood-state blood sample and to take, from the blood sample, a sample for the electrical characteristic measurement. Thereafter, it is necessary to close the lid and to subject the vessel to the separation step. In this case, therefore, it is necessary to provide a recapper device for opening and closing the lid of the vessel, which leads to increases in the device manufacturing cost and the device running cost.

It is therefore a principal object of the present technology to provide a technique that allows obtaining information on a blood sample from an electrical characteristic of the blood sample even when it is introduced in an existing blood test system.

Solutions to Problems

Specifically, the present technology provides an electrical characteristic measurement device for measuring an electrical characteristic of a blood sample, the device including: a mixing unit configured to mix a blood cell component and a plasma component on the basis of the composition ratio between the blood cell component and the plasma component in a blood sample; and a blood sample measurement unit configured to measure an electrical characteristic of a blood sample obtained by mixing by the mixing unit.

The electrical characteristic measurement device according to the present technology may further include a blood component ratio measurement unit configured to measure the composition ratio between the blood cell component and the plasma component in the blood sample.

In the electrical characteristic measurement device according to the present technology, the blood component ratio measurement unit may include an optical detector configured to detect the boundary surface between the blood cell component and the plasma component.

In the electrical characteristic measurement device according to the present technology, the blood component ratio measurement unit may include an electrical detector configured to detect the boundary surface between the blood cell component and the plasma component.

In the electrical characteristic measurement device according to the present technology, the blood sample measurement unit may also be configured to measure the permittivity of the blood sample.

The electrical characteristic measurement device according to the present technology may further include a blood condition analysis unit configured to analyze the condition of the blood sample on the basis of an electrical characteristic of the blood sample obtained by mixing by the mixing unit.

The electrical characteristic measurement device according to the present technology may further include a correction unit configured to correct the result of measurement of an electrical characteristic of the blood sample in accordance with the composition ratio of the plasma component.

The electrical characteristic measurement device according to the present technology may further include a plasma examination unit configured to examine the plasma component.

The electrical characteristic measurement device according to the present technology may further include a separation unit configured to separate the plasma component and the blood cell component.

Next, the present technology provides an electrical characteristic measurement method for measuring an electrical characteristic of a blood sample, the method including: a mixing step including mixing a blood cell component and a plasma component on the basis of the composition ratio between the blood cell component and the plasma component in a blood sample; and a blood sample measurement step including measuring an electrical characteristic of a blood sample obtained by mixing by the mixing step.

The present technology further provides a blood condition analysis system for analyzing the condition of a blood sample, the system including: an electrical characteristic measurement device including a mixing unit configured to mix a blood cell component and a plasma component on the basis of the composition ratio between the blood cell component and the plasma component in a blood sample and a blood sample measurement unit configured to measure an electrical characteristic of a blood sample obtained by mixing by the mixing unit; and a blood condition analysis device including a blood condition analysis unit configured to analyze the condition of the blood sample on the basis of an electrical characteristic of the blood sample obtained by mixing by the mixing unit.

The blood condition analysis system according to the present technology may further include a server configured to store the result of measurement by the electrical characteristic measurement device and/or the result of analysis by the blood condition analysis device.

In addition, the present technology provides an electrical characteristic measurement program for use in measuring an electrical characteristic of a blood sample, the program being configured to implement a mixing function for mixing a blood cell component and a plasma component on the basis of the composition ratio between the blood cell component and the plasma component in a blood sample and a blood sample measurement function for measuring an electrical characteristic of a blood sample obtained by mixing by the mixing function.

Effects of the Invention

When introduced in an existing blood test system, the present technology allows obtaining information on a blood sample from an electrical characteristic of the blood sample.

It will be understood that the effects described herein are non-limiting and the present technology may bring about any of the effects described herein.

MODE FOR CARRYING OUT THE INVENTION

Figure 1:
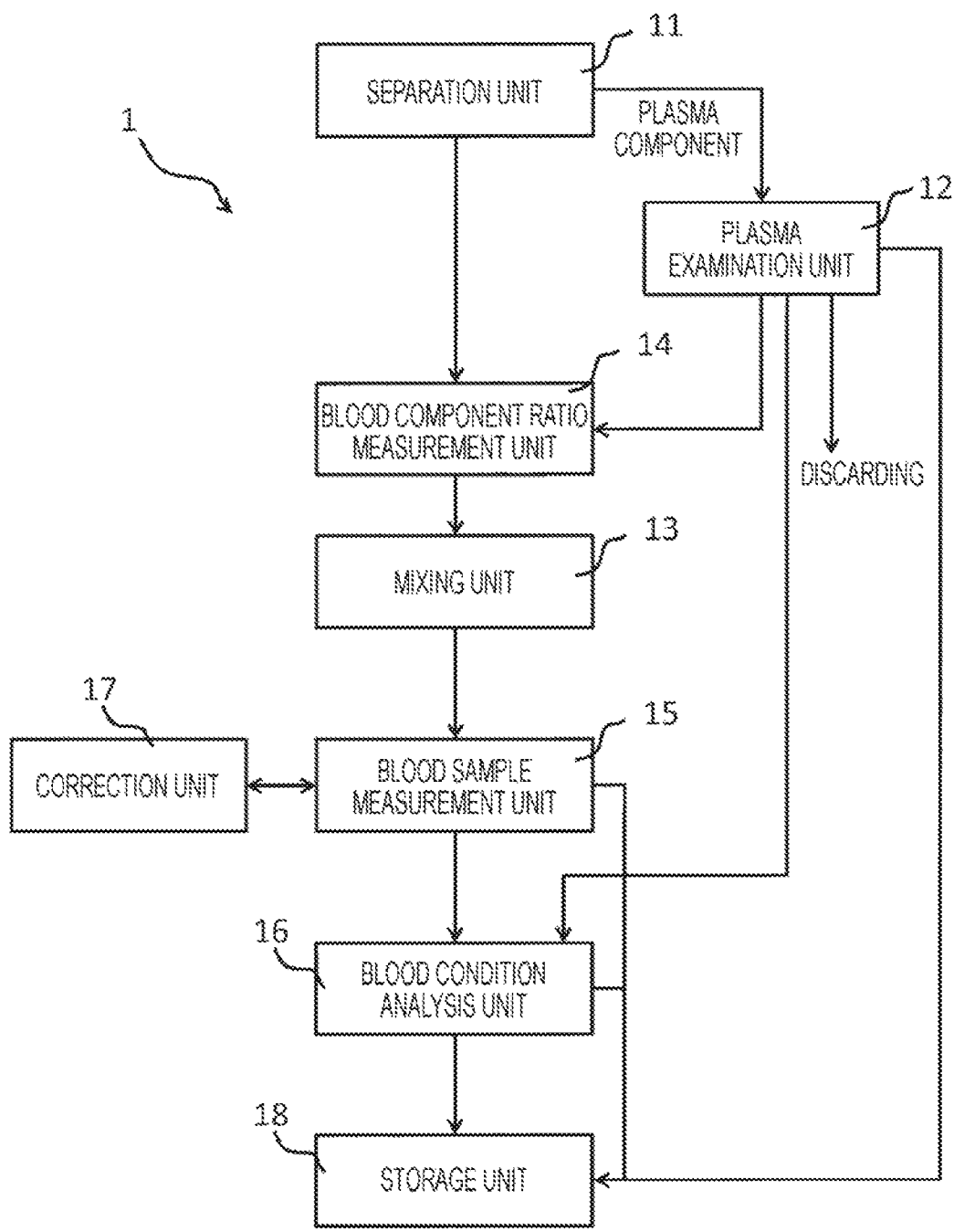
FIG. 1 is a schematic conceptual diagram schematically showing the concept of an electrical characteristic measurement device 1 according to the present technology.

Hereinafter, preferred modes for carrying out the present technology will be described with reference to the drawings. It will be understood that the embodiments described below are mere typical embodiments of the present technology and should not be construed as limiting the scope of the present technology. Meanwhile, descriptions will be provided in the following order.

1. Electrical characteristic measurement device 1
(1) Separation unit 11
(2) Plasma examination unit 12
(3) Mixing unit 13
(4) Blood component ratio measurement unit 14
(5) Blood sample measurement unit 15
(6) Blood condition analysis unit 16
(7) Correction unit 17
(8) Storage unit 18
(9) Blood sample
2. Blood condition analysis system 10
(1) Electrical characteristic measurement device 1
(2) Blood condition analysis device 101
(3) Server 102
(4) Display unit 103
(5) User interface 104
3. Electrical characteristic measurement method
(1) Separation step I
(2) Plasma examination step II
(3) Mixing step III
(4) Blood component ratio measurement step IV
(5) Blood sample measurement step V (6) Blood condition analysis step VI
(7) Correction step VII
(8) Storage step VIII
4. Electrical characteristic measurement program
1. Electrical Characteristic Measurement Device 1

FIG. 1 is a schematic conceptual diagram schematically showing the concept of an electrical characteristic measurement device 1 (hereinafter also referred to as the "device 1") according to the present technology. The electrical characteristic measurement device 1 according to the present technology is configured to measure an electrical characteristic of a blood sample including a blood cell component and a plasma component (hereinafter such a blood sample is also simply referred to as a "blood sample") and includes at least a mixing unit 13 and a blood sample measurement unit 15. If necessary, the device 1 may also include a separation unit 11, a plasma examination unit 12, a blood component ratio measurement unit 14, a blood condition analysis unit 16, a correction unit 17, a storage unit 18, and other units. Hereinafter, each unit will be described in detail. Note that hereinafter, the respective units will be described almost in order of blood test steps performed generally, but not all the units are necessary for the present technology.

(1) Separation Unit 11

Some of various blood tests on blood samples containing a blood cell component and a plasma component are performed using a plasma component. In a case where such blood tests are performed, the blood sample is generally separated into a blood cell component and a plasma component in advance.

If necessary, the electrical characteristic measurement device 1 according to the present technology may include a separation unit 11 configured to separate a whole-blood-state blood sample into a blood cell component and a plasma component. On the other hand, the electrical characteristic measurement device 1 according to the present technology does not have to include the separation unit 11 and may be designed to use a blood sample obtained by separation into a blood cell component and a plasma component using other means.

The separation unit 11 is configured to separate a whole-blood-state blood sample into a blood cell component and a plasma component. The separation may be performed by any method freely selected from known separation methods. Examples of the separation method include a separation method including allowing a whole blood sample to stand for a certain period of time in a blood-collecting vessel containing an anticoagulant; and a method of centrifuging a blood-collecting vessel containing a whole blood sample.

(2) Plasma Examination Unit 12

The electrical characteristic measurement device 1 according to the present technology may include a plasma examination unit 12 configured to examine the condition of a blood sample using the plasma component separated by the separation unit 11 or other means. The plasma examination unit 12 is not indispensable in the electrical characteristic measurement device 1 according to the present technology. Alternatively, the examination using the plasma component may be performed using an external plasma examination device connected to the measurement device.

The plasma examination unit 12 is configured to perform a known examination method using plasma. Examples of such a known method include a method including adding calcium and tissue thromboplastin to plasma and measuring prothrombin time (PT); a method including adding contact factor activators such as partial thromboplastin and calcium to plasma and measuring activated partial thromboplastin time (APTT); and a method of determining the concentration of ammonia in plasma. In a case where the physical properties of the plasma component are changed by performing the examination as mentioned above, the plasma component will be discarded. On the other hand, in a case where the physical properties of the plasma component are not changed by the examination performed by the plasma examination unit 12, a method of returning the plasma component to the blood sample may also be performed.

(3) Mixing Unit 13

The mixing unit 13 is configured to mix the blood cell component and the plasma component, which have been separated by the separation unit 11 or other means. Specifically, the blood cell component and the plasma component are mixed on the basis of the composition ratio between the blood cell component and the plasma component in the blood sample.

The mixing unit 13 may use any mixing method freely selected from known mixing methods as long as the effect of the present technology is not impaired. Examples of mixing methods include mixing by pipetting, mixing using a mixing rod or other means, and mixing by turning upside down the vessel containing the blood sample. In the present technology, it is preferable to adopt mixing by pipetting in view of, for example, suppression of scattering of the blood sample and suppression of activation of platelets and other components in the blood sample.

In some cases, for example, the plasma component is sampled from the blood sample by the plasma examination unit 12 before the blood cell component and the plasma component are mixed by the mixing unit 13. In such cases, the plasma component ratio is lowered. If the blood cell component and the plasma component are mixed under such conditions, the hematocrit value will differ between the mixed blood sample and the whole-blood-state blood sample obtained before the separation step is performed. As a result, there will be a discrepancy between the result of measurement of an electrical characteristic of the blood sample having undergone the separation step and the result of measurement of an electrical characteristic of the blood sample not having undergone the separation step. In the following description, for the sake of convenience, the whole-blood-state blood sample obtained before the separation step will be referred to as the "whole blood sample".

Therefore, the mixing unit 13 preferably has a dispensing mechanism configured to dispense blood samples according to the composition ratio between the blood cell component and the plasma component separated from each other.

The following are examples of the dispensing method based on the composition ratio between the blood cell component and the plasma component in the blood sample.

For example, in a case where the ratio of the plasma component is lower than that in the whole blood sample, the dispensing method may include sucking a predetermined amount of the blood component from the liquid phase of the blood cell component using a pipette to achieve the same composition ratio between the blood cell component and the plasma component as that in the whole blood sample. On the other hand, in a case where the ratio of the blood cell component is lower than that in the whole blood sample, the dispensing method may include sucking a part of the plasma component to achieve the same composition ratio between the blood cell component and the plasma component as that in the whole blood sample.

Alternatively, the dispensing method may include sucking a predetermined amount from each of the liquid phase of the blood cell component and the liquid phase of the plasma component using a pipette to newly form a blood sample with the same composition ratio between the blood cell component and the plasma component as that in the whole blood sample.

In this regard, the above dispensing method is performed in such a manner that the composition ratio between the blood cell component and the plasma component in the mixed blood sample becomes the same as that in the whole blood sample. Alternatively, the dispensing method may include dispensing a plasma component, a blood cell component, or both of them to achieve the desired hematocrit value instead of dispensing to achieve the same composition ratio between the plasma component and the blood cell component as that in the whole blood sample.

On the other hand, in a case where the composition ratio between the blood cell component and the plasma component in the blood sample having undergone the separation step is the same as that in the whole blood sample, the method used in the electrical characteristic measurement device 1 according to the present technology may include mixing the blood cell component and the plasma component, regardless of the composition ratio, to form whole blood.

(4) Blood Component Ratio Measurement Unit 14

The blood component ratio measurement unit 14 is configured to measure the composition ratio between the blood cell component and the plasma component in the blood sample before the blood cell component and the plasma component are mixed by the mixing unit 13. Although not indispensable in the electrical characteristic measurement device 1 according to the present technology, the blood component ratio measurement unit 14 is preferably provided in order to improve the analysis accuracy.

The blood component ratio measurement unit 14 may measure the composition ratio by using any method freely selected from known methods as long as the effect of the present technology is not impaired. For example, the measurement method may include detecting the boundary surface between the blood cell component and the plasma component separated from each other and determining the composition ratio on the basis of the detection result.

Hereinafter, a specific example of the method of measuring the composition ratio will be described with reference to FIGS. 2 and 3. The method of detecting the boundary surface between the blood cell component and the plasma component may be any method freely selected from various methods. The example shown in FIGS. 2 and 3 employs an optical measurement method.

Figure 2:
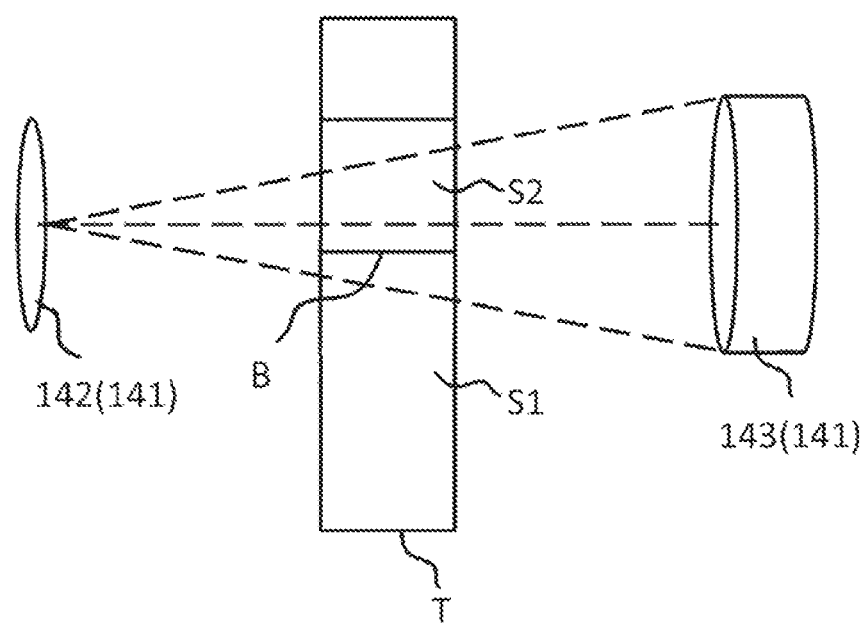
FIG. 2 is a conceptual diagram showing an example of a blood component ratio measurement unit employing an optical measurement method.

In the example shown in FIG. 2, the blood component ratio measurement unit 14 has an optical detector 141 configured to detect the boundary surface B between the blood cell component S1 and the plasma component S2. The optical detector 141 is configured to detect the boundary surface B on the basis of the fractions of specific light passing through the blood cell component S1 and the plasma component S2, in other words, light transmittances. The optical detector 141 includes a light application unit 142 configured to apply the light and a light detection unit 143 configured to acquire voltage signals on the basis of the light applied from the light application unit 142.

The light source of the light application unit 142 may be of any type with no influence on the physical properties of the blood sample, which may be, for example, a semiconductor laser, specifically, a laser diode, a solid laser, or a gas laser. In particular, using a semiconductor laser can make the device compact and inexpensive.

The light detection unit 143 is disposed at a position facing the light application unit 142 with a container T such as a blood-collecting vessel containing the blood sample placed between them, and provided to detect the light applied from the light application unit 142. The mode of the light detection unit 143 is not limited and may be appropriately set according to the type of light applied from the light application unit 142. The light detection unit 143 may also include a light separation element, a fluorescence detection section, a scattered light detection section, and other sections for use in common light detecting means.

In the blood component ratio measurement unit 14 having the optical detector 141, for example, white light is applied from the light application unit 142 toward the light detection unit 143. In such a case, the plasma component S2 has a relatively high light transmittance value. On the other hand, the blood cell component S1 has a light transmittance value lower than that of the plasma component.

Figure 3:
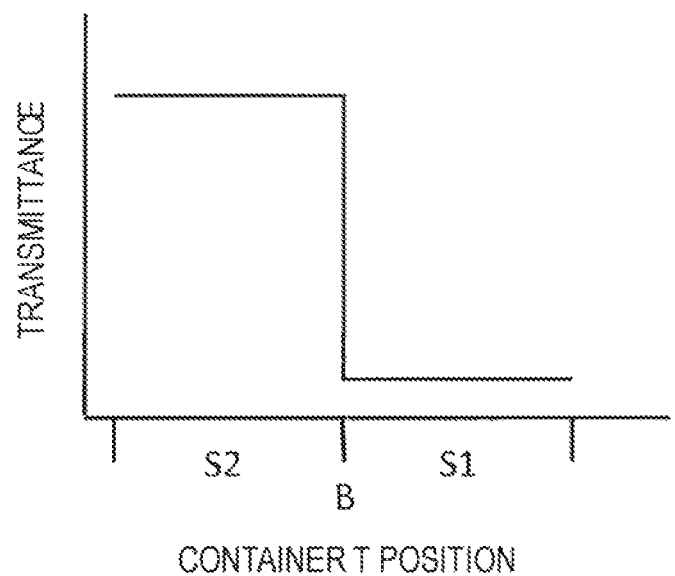
FIG. 3 is a drawing-substitute graph showing the result obtained by the blood component ratio measurement unit shown in FIG. 2.

Then, in a case where the blood component ratio measurement unit 14 having the optical detector 141 as mentioned above is moved upward and downward relative to the container T, such as a blood-collecting vessel, containing the blood sample, the white light transmittance significantly changes as shown in FIG. 3 before and after the white light passes through the boundary surface B, so that the boundary surface B can be clearly detected.

The blood component ratio measurement unit 14 shown in FIG. 2 is configured to detect the boundary surface B using light transmittance as an index. Alternatively, the optical measurement method may include detecting the boundary surface B using, for example, absorbance as an index. Another optical measurement method may also be used, including applying light to the container T, capturing an image capable of indicating the boundary surface B, and determining the blood component ratio from the captured image. In this case, the imaging method is not limited and may be any known imaging method, such as a method including: providing the light application unit 142 with a light source array having one or more light sources; further providing the light detection unit 143 with a light source array having one or more light sources; and detecting the boundary surface B using the light source arrays.

The blood component ratio measurement unit 14 suitable for use in the electrical characteristic measurement device 1 according to the present technology may also use an electrical measurement method to detect the boundary surface B. Hereinafter, an example of the blood component ratio measurement unit 14 designed to use an electrical measurement method will be described with reference to FIGS. 4 and 5.

Figure 4:
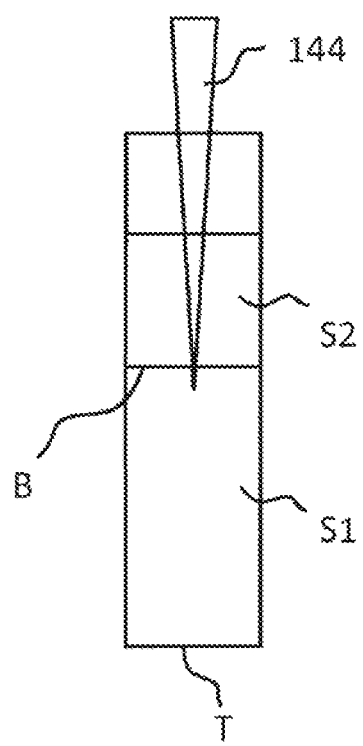
FIG. 4 is a conceptual diagram showing an example of a blood component ratio measurement unit employing an electrical measurement method.

In the example shown in FIG. 4, the blood component ratio measurement unit 14 has an electrical detector 144 configured to detect the boundary surface B between the blood cell component S1 and the plasma component S2. The electrical detector 144 has a pipetter and a tip attached to the front end of the pipetter, in which the tip is made of a conductive material. The tip may be made of any material having electrical conductivity, such as a carbon black-containing, homopolymer-type polypropylene material.

In this regard, in the blood sample, the plasma component S2, which is composed mainly of water, has a relatively high conductivity value. On the other hand, the blood cell component S1, which is composed mainly of erythrocytes, has a relatively low conductivity value.

Figure 5:
FIG. 5 is a drawing-substitute graph showing the result obtained by the blood component ratio measurement unit shown in FIG. 4.

Then, in a case where the blood component ratio measurement unit 14 having the electrical detector 144 is moved upward and downward relative to the container T, the conductivity significantly changes as shown in FIG. 5 before and after the electrical detector 144 passes through the boundary surface B, so that the boundary surface B can be clearly detected.

In this case, in the electrical characteristic measurement device 1 according to the present technology, the blood component ratio measurement unit 14 having the electrical detector 144 may be configured to function as the mixing unit 13. Specifically, in a case where the electrical detector 144 includes a pipetter and a tip attached to the front end thereof, the blood cell component S1 and the plasma component S2 can be mixed using the pipetter. In this case, the pipetter and the tip function as the mixing unit 13 and the blood component ratio measurement unit 14, which makes it possible to downsize the electrical characteristic measurement device 1 and to reduce the device 1 production cost.

In this case, the blood component ratio measurement unit 14 shown in FIG. 4 is configured to detect the boundary surface B using conductivity as an index. Alternatively, the boundary surface B may be detected using, for example, permittivity, impedance, admittance, capacitance, or conductance as an index.

(5) Blood Sample Measurement Unit 15

The blood sample measurement unit 15 is configured to measure an electrical characteristic of the whole-blood-state blood sample prepared by mixing the blood cell component S1 and the plasma component S2 by the mixing unit 13.

Examples of the electrical characteristic that can be measured by the electrical characteristic measurement device 1 according to the present technology include permittivity, impedance, admittance, capacitance, conductance, conductivity, and phase angle. These electrical characteristics can be converted to one another by the mathematical formulas shown in Table 1 below. Therefore, for example, the evaluation result obtained by evaluating the hematocrit value and/or the hemoglobin amount using the result of permittivity measurement of a blood sample will be the same as the evaluation result obtained using the result of impedance measurement of the same blood sample. Many of these electrical quantities and physical property values can be expressed using complex numbers, which will simplify the conversion formulas. In addition, the frequency band for use in the electrical measurement by the blood sample measurement unit 15 may be appropriately selected according to the condition of the blood sample to be measured, the purpose of the measurement, or other factors.

TABLE 1

<Major interchangeable electrical quantities and physical property values>

| Electrical quantities and physical property values | Symbol | Complex number expression |
|---|---|---|
| Voltage | V | $V^* = \|V\|\exp j(\omega t + \phi)$ |
| Current | I | $I^* = \|I\|\exp j(\omega t + \varphi)$ |
| Impedance | Z | $Z^* = R + jX$ (R: Resistance, X: Reactance) |
| Admittance | Y | $Y^* = G + jB$ (G: Conductance, B: Susceptance) |
| Capacitance | C | $C^* = C - jG/\omega$ |
| Conductance | G | $G^* = G + j\omega C$ |
| Loss tangent (Dielectric loss tangent) | D or tan δ | |
| Loss angle | δ | |
| Phase angle | θ | |
| Q value | Q | |
| Permittivity | ε | $\varepsilon^* = \varepsilon - j\kappa/\omega\varepsilon_0$ |
| Conductivity | κ | $\kappa^* = \kappa + j\omega\varepsilon_0\varepsilon$ |

<Mathematical Formulas Associating Respective Electrical Quantities and Physical Property Values>

$$Z^* = V^*/I^*$$

$$\theta = \phi - \varphi$$

$$Y^* = 1/Z^*$$

$$C = B/\omega$$

$$D = \tan \delta = G/\omega C = 1/Q$$

$$\varepsilon^* = C^*/C_0$$

$$K^* = j\omega\varepsilon_0\varepsilon^*$$

ω: Angular frequency
$\varepsilon_0$: Vacuum permittivity (constant)
$C_0$: Constant depending on measurement device or other factors Values with *: Complex numbers The blood sample measurement unit 15 may include one or more blood sample holders. The blood sample holder is not indispensable in the electrical characteristic measurement device 1. Alternatively, the blood sample measurement unit 15 may also be so designed that, for example, a known cartridge type measurement container can be attached to it.

In the case where the blood sample measurement unit 15 has a blood sample holder, the blood sample holder may be designed in any desired form capable of holding, in the blood sample measurement unit 15, the blood sample to be measured. For example, one or more cells may be provided on a substrate to function as the blood sample holders, or one or more containers may be provided to function as the blood sample holders.

In the case where one or more containers are used as the blood sample holders, the containers may be in any form capable of holding the blood sample to be measured, such as a cylindrical form, a polygonal tube form with a polygonal cross-section (a triangular, quadrangular, or polygonal cross-section), a conical form, a polygonal pyramid form with a polygonal cross-section (a triangular, quadrangular, or polygonal cross-section), or a combination of one or more thereof, which may be freely designed according to the condition of the blood sample, the measurement method, or other conditions.

Also, the material used to form the container is not limited, and may be freely selected within a range where there is no influence on the condition of the blood sample to be measured, the measurement purpose, and other conditions. In the present technology, a resin is particularly preferably used to form the container in view of ease of forming or molding and other features. In the present technology, the usable resin may be of any type, and one or more resins suitable for use in holding the blood sample may be freely selected and used. Examples of such resins include hydrophobic and insulating polymers or copolymers, such as polypropylene, polymethyl methacrylate, polystyrene, acrylic, polysulfone, and polytetrafluoroethylene, and polymer blends. Among them, one or more resins selected from polypropylene, polystyrene, acrylic, and polysulfone are particularly preferably used to form the blood sample holder in the present technology. This is because these resins have the property of being less likely to cause blood clots.

The blood sample holder is preferably so designed that it can be air-tightly closed while holding the blood sample. However, the blood sample holder does not need to be in an air-tight form if the blood sample can be kept stable with no influence on the measurement during the time period required for the measurement of the electrical characteristic of the blood sample.

Any specific method may be selected depending on the form of the blood sample holder and used to introduce the blood sample into the blood sample holder and to air-tightly close the holder. Examples of such a method include a method including providing a lid for the blood sample holder, introducing the blood sample into the blood sample holder with a pipette or other means, and then closing the lid to air-tightly close the blood sample holder; and a method including inserting an injection needle into the blood sample holder through its outer surface, injecting the blood sample into the blood sample holder, and then sealing, with grease or other materials, the portion through which the needle has passed.

The blood sample measurement unit 15 may include one or more energization sections. The energization section is not indispensable in the electrical characteristic measurement device 1. Alternatively, for example, the blood sample holder may be so designed that electrodes can be inserted into the blood sample holder from the outside so that an external energization device can be used.

The energization section is configured to apply a predetermined voltage to the blood sample at respective preset measurement intervals from the start time at which the energization section receives an instruction to start the measurement or at which the electrical characteristic measurement device 1 is turned on.

The electrodes used as parts of the energization section may be formed in any number and made of any material as long as the effect of the present technology is not impaired. The electrodes may include, for example, titanium, aluminum, stainless steel, platinum, gold, copper, graphite, or other materials. Among them, in the present technology, an electrically conductive material containing titanium is particularly preferably used to form the electrodes. This is because titanium has the property of being less likely to cause blood clots.

The blood sample measurement unit 15 may also be configured to perform a plurality of measurements. The method of performing a plurality of measurements may be, for example, a method of simultaneously performing a plurality of measurements with a plurality of blood sample measurement units 15 provided therefor, a method of performing a plurality of measurements by scanning with one blood sample measurement unit 15, a method of moving the blood sample holder to perform a plurality of measurements, or a method of selecting, by switching, one or more blood sample measurement units 15 for the actual measurement from a plurality of blood sample measurement units 15.

Blood samples can significantly vary in electrical characteristic such as permittivity as the temperature changes. Therefore, the blood sample measurement unit 15 preferably has a temperature control function, which can prevent temperature change-induced measurement errors.

(6) Blood Condition Analysis Unit 16

The blood condition analysis unit 16 is configured to analyze the condition of blood on the basis of the electrical characteristic of the blood sample prepared by mixing by the mixing unit 13. The blood condition analysis unit 16 is not indispensable in the electrical characteristic measurement device 1 according to the present technology. Alternatively, an external analysis device or other devices may be used to analyze the condition of the blood sample on the basis of the measurement results obtained by the electrical characteristic measurement device 1 according to the present technology.

In addition, if necessary, the blood condition analysis unit 16 may also be configured to detect the result of examination by the plasma examination unit 12, the result of measurement by the blood sample measurement unit 15, and other information and to analyze the condition of blood on the basis of the results.

The blood condition that can be analyzed by the blood condition analysis unit 16 of the electrical characteristic measurement device 1 according to the present technology may be any phenomenon in which changes in the electrical characteristic of the blood sample can be observed as a result of changes in blood condition. In addition, changes in various conditions may be analyzed and evaluated. Examples of such a phenomenon include blood coagulation (blood clotting), fibrin formation, fibrin clot formation, clot formation, platelet aggregation, erythrocyte rouleaux formation, blood agglutination, erythrocyte sedimentation (blood sedimentation), clot retraction, hemolysis such as fibrinogenolysis, and fibrinolysis.

(7) Correction Unit 17

The electrical characteristic measurement device 1 according to the present technology may include a correction unit 17 configured to correct the result of measurement by the blood sample measurement unit 15. The correction unit 17 is not indispensable in the electrical characteristic measurement device 1 according to the present technology. Alternatively, an external measurement result correction device may be connected to correct the result of measurement by the blood sample measurement unit 15.

In the electrical characteristic measurement device 1 according to the present technology, for example, the plasma examination unit 12 may take a sample from the plasma component, and then the blood cell component and the remaining plasma component may be mixed. In this case, the mixed blood sample will differ in hematocrit value from the whole blood sample. As a result, there will be a discrepancy between the result of measurement of the electrical characteristic of the mixed blood sample and the result of measurement of the electrical characteristic of the whole blood sample.

Therefore, the correction unit 17 is configured to detect the measurement result on the composition ratio between the blood cell component and the plasma component in the blood sample measured by the blood component ratio measurement unit 14 or to detect the measurement result on the electrical characteristic of the whole blood sample and to correct the result of measurement of the electrical characteristic by the blood sample measurement unit 15 on the basis of the detected result. Specifically, the correction is performed in such a manner that the result of measurement of the electrical characteristic by the blood sample measurement unit 15 becomes equivalent to the result of measurement of the electrical characteristic of the whole blood sample.

To perform the correction, the correction unit 17 may use any method freely selected from known correction methods as long as the effect of the present technology is not impaired.

In this regard, it is known that the result of evaluation of the coagulability of a blood sample is greatly influenced by the fact that at the time of measurement, a drug is concentrated into the plasma component by the excluded volume effect of the blood cell component in the blood sample. In addition, it is known that the results of evaluation of the coagulability of blood samples can differ depending on the amount of hemoglobin in the blood samples, even when the blood samples are taken from the same subject. Therefore, the correction method may include, for example, measuring in advance the residual amount of the drug and the amount of hemoglobin in the blood sample and correcting the result of measurement of the electrical characteristic of the blood sample on the basis of the measured values.

In the present technology, the correction unit is used to correct the result of measurement of the electrical characteristic of the blood sample. Alternatively, for example, the amount of addition of the drug used in the examination may be controlled so that there will be no need for correction when the electrical characteristic of the blood sample is measured.

(8) Storage Unit 18

The electrical characteristic measurement device 1 according to the present technology may include a storage unit 18 configured to store the result of each analysis by the plasma examination unit 12, the result of each analysis by the blood condition analysis unit 16, the result of measurement by the blood sample measurement unit 15, and other information. The storage unit 18 is not indispensable in the electrical characteristic measurement device 1 according to the present technology. Alternatively, an external storage device may be connected to store each result.

In the electrical characteristic measurement device 1 according to the present technology, the storage unit 18 may be provided separately for each unit, or the electrical characteristic measurement device 1 may be so designed that various results obtained by the respective units are stored in one storage unit 18.

(9) Blood Sample

Any blood sample containing at least a blood cell component and a plasma component may be freely selected and measured by the electrical characteristic measurement device 1 according to the present technology. Specific examples of the blood sample include whole blood or a dilution thereof, and blood samples containing any of various reagents or drugs such as anticoagulation stopping agents, coagulation activators, anticoagulants, platelet activators, and antiplatelet agents.

As described above, the electrical characteristic measurement device 1 according to the present technology includes the mixing unit 13 and the blood sample measurement unit 15. Therefore, even when an existing blood test system is used, with which a whole blood sample is subjected to a separation step in advance, the blood sample can be introduced into the electrical characteristic measurement device 1, by which information about the blood sample can be obtained from the electrical characteristic of the blood sample.

On the other hand, when a blood sample containing a blood cell component and a plasma component separated from each other is mixed to form a whole blood state again, a recapper can be introduced so that after sampling from the plasma component, the vessel such as the blood-collecting vessel can be recapped and then subjected to the mixing step.

In this case, however, the necessary introduction of the recapper will increase the device production cost and the device running cost.

In contrast, the electrical characteristic measurement device 1 according to the present technology, which has the mixing unit 13, does not require opening and closing the lid of the vessel such as the blood-collecting vessel, which makes it possible to reduce the cost of manufacture of the electrical characteristic measurement device 1.

In addition, the mixing unit 13 in the electrical characteristic measurement device 1 according to the present technology is configured to mix the blood cell component S1 and the plasma component S2 on the basis of the composition ratio between the blood cell component S1 and the plasma component S2 in the blood sample. This feature can minimize the possibility of occurrence of a discrepancy between the result of measurement of the electrical characteristic of the blood sample having undergone the separation step and the result of measurement of the electrical characteristic of the blood sample not having undergone the separation step, for example, when the blood cell component S1 and the plasma component S2 are dispensed from the blood sample having undergone the separation step.

In addition, the electrical characteristic measurement device 1 according to the present technology, which has the mixing unit 13 configured to mix the blood cell component and the plasma component on the basis of the composition ratio between the blood cell component S1 and the plasma component S2 in the blood sample, makes it possible to newly prepare a blood sample having any desired hematocrit value. As a result, the condition of the blood sample, particularly, the coagulability of the blood sample can be accurately analyzed without taking into account the influence of the hematocrit value.

It will be understood that the effects described herein are only by way of example and that the present technology may bring about any of the effects described herein.

2. Blood Condition Analysis System 10

Figure 6:
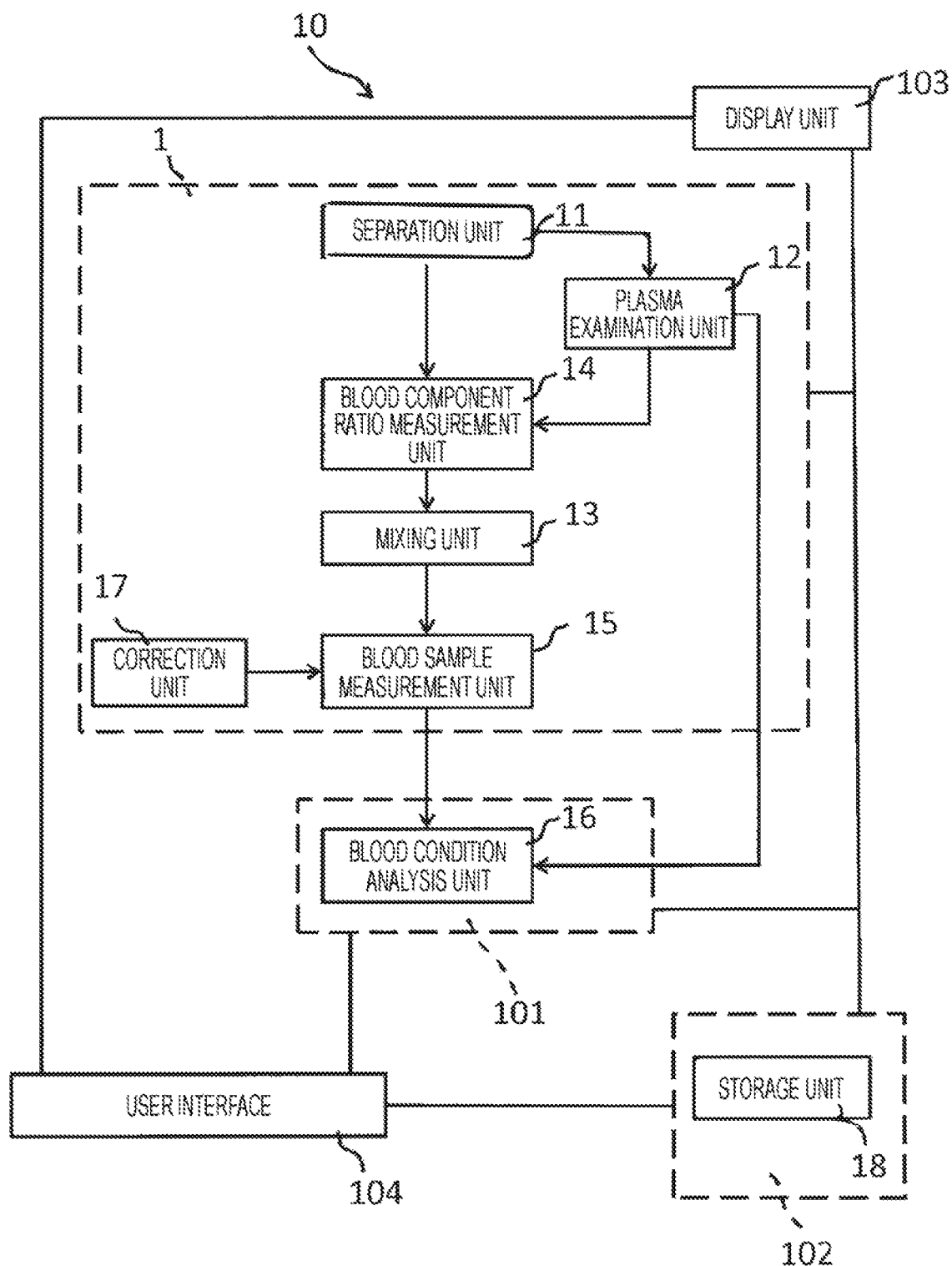
FIG. 6 is a schematic conceptual diagram schematically showing the concept of a blood condition analysis system according to the present technology.

FIG. 6 is a schematic conceptual diagram schematically showing the concept of a blood condition analysis system 10 according to the present technology. The blood condition analysis system 10 according to the present technology includes at least an electrical characteristic measurement device 1 and a blood condition analysis device 101, which are major components. In addition, if necessary, the system 10 may also include, for example, a server 102, a display unit 103, and a user interface 104. Hereinafter, each component will be described in detail.

(1) Electrical Characteristic Measurement Device 1

The electrical characteristic measurement device 1 includes at least a mixing unit 13 and a blood sample measurement unit 15. In addition, if necessary, the electrical characteristic measurement device 1 may include, for example, a separation unit 11, a plasma examination unit 12, a blood component ratio measurement unit 14, and a correction unit 17. In this regard, each component of the electrical characteristic measurement device 1 is the same as that of the electrical characteristic measurement device 1 described above, and, therefore, the description thereof is omitted here.

(2) Blood Condition Analysis Device 101

The blood condition analysis device 101 includes a blood condition analysis unit 16 configured to analyze the condition of the blood sample on the basis of an electrical characteristic of the blood sample prepared by mixing by the mixing unit 13. In this regard, the blood condition analysis unit 16 is the same as the blood condition analysis unit 16 of the electrical characteristic measurement device 1 described above, and, therefore, the description thereof is omitted here.

(3) Server 102

The server 102 includes a storage unit 18 configured to store the result of measurement by the electrical characteristic measurement device 1 and/or the result of analysis by the blood condition analysis device 101. The details of the storage unit 18 are the same as those of the storage unit 18 in the electrical characteristic measurement device 1 described above.

(4) Display Unit 103

The display unit 103 is configured to display, for example, the result of measurement by the electrical characteristic measurement device 1 and/or the result of analysis by the blood condition analysis device 101. A plurality of display units 103 may be provided for the respective data or results to be displayed, or one display unit 103 may be provided to display all data or results.

(5) User Interface 104

The user interface 104 is a section provided for user operation. The user can access each component of the blood condition analysis system 10 according to the present technology through the user interface 104.

In the blood condition analysis system 10 according to the present technology described above, the electrical characteristic measurement device 1, the blood condition analysis device 101, the server 102, the display unit 103, and the user interface 104 may be connected to one another via a network.

3. Electrical Characteristic Measurement Method

Figure 7:
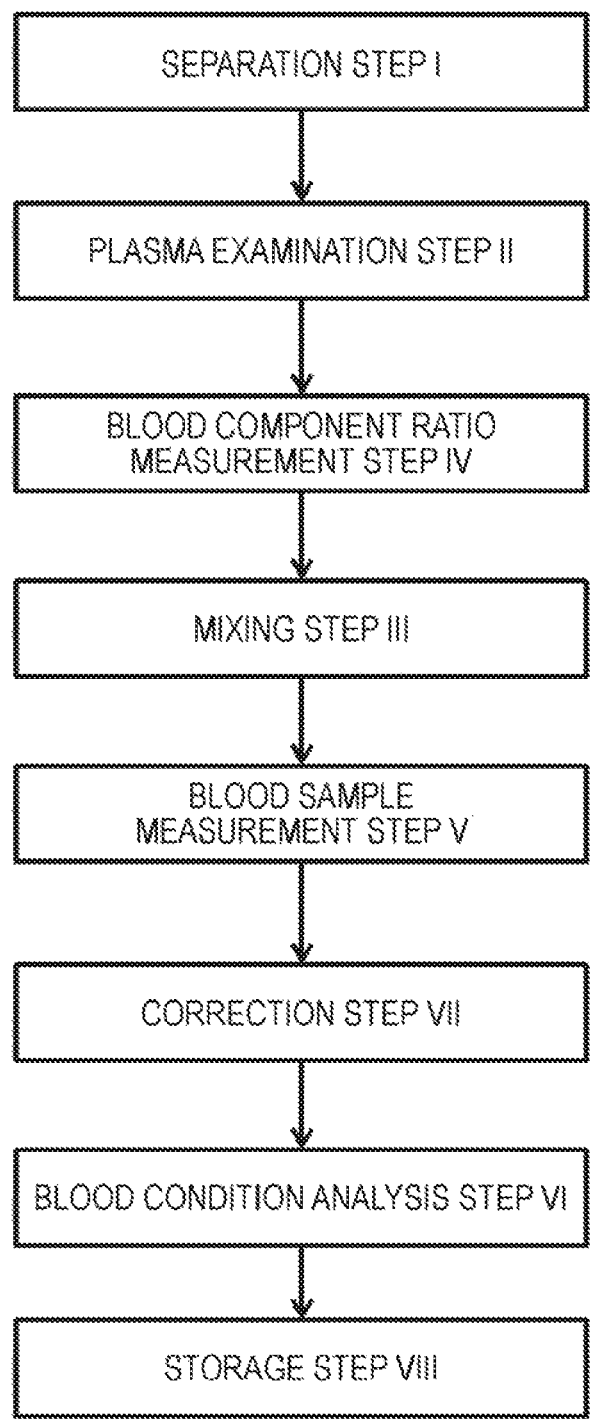
FIG. 7 is a flowchart of an electrical characteristic measurement method according to the present technology.

FIG. 7 is a flowchart of the electrical characteristic measurement method according to the present technology. The electrical characteristic measurement method according to the present technology is a method of measuring an electrical characteristic of a blood sample and includes at least a mixing step III and a blood sample measurement step V. In addition, if necessary, the electrical characteristic measurement method according to the present technology may include, for example, a separation step I, a plasma examination step II, a blood component ratio measurement step IV, a blood condition analysis step VI, a correction step VII, and a storage step VIII. Hereinafter, each step will be described in detail.

(1) Separation Step I

The separation step I includes separating a whole-blood-state blood sample into a blood cell component and a plasma component after blood sampling. The separation step I is not indispensable in the electrical characteristic measurement method according to the present technology. Alternatively, another device may be used to separate a whole-blood-state blood sample into a blood cell component and a plasma component after blood sampling. The details of the separation method performed in the separation step I are the same as those of the separation method performed by the separation unit 11 of the electrical characteristic measurement device 1 described above. Therefore, the description thereof is omitted here.

(2) Plasma Examination Step II

The plasma examination step II includes examining the condition of the blood sample using, for example, the plasma component separated by the separation step I. The plasma examination step II is not indispensable in the electrical characteristic measurement method according to the present technology. Alternatively, an external device or method may also be used to examine the separated plasma component. The details of the examination method performed in the plasma examination step II are the same as those of the examination method performed by the plasma examination unit 12 of the electrical characteristic measurement device 1 described above. Therefore, the description thereof is omitted here.

(3) Mixing Step III

The mixing step III includes, for example, mixing the blood cell component and the plasma component separated by the separation step I. The details of the mixing method performed in the mixing step III are the same as those of the mixing method performed by the mixing unit 13 of the electrical characteristic measurement device 1 described above. Therefore, the description thereof is omitted here.

(4) Blood Component Ratio Measurement Step IV

The blood component ratio measurement step IV includes measuring the composition ratio between the blood cell component and the plasma component in the blood sample before the blood cell component and the plasma component are mixed by the mixing step III. The blood component ratio measurement step IV is not indispensable in the electrical characteristic measurement method according to the present technology. Alternatively, an external device or method may also be used to measure the composition ratio between the blood cell component and the plasma component.

The details of the measurement method performed in the blood component ratio measurement step IV are the same as those of the measurement method performed by the blood component ratio measurement unit 14 of the electrical characteristic measurement device 1 described above. Therefore, the description thereof is omitted here.

(5) Blood Sample Measurement Step V

The blood sample measurement step V includes measuring an electrical characteristic of the whole-blood-state blood sample obtained by mixing the blood cell component and the plasma component by the mixing step III.

The details of the measurement method performed in the blood sample measurement step V are the same as those of the measurement method performed by the blood sample measurement unit 15 of the electrical characteristic measurement device 1 described above. Therefore, the description thereof is omitted here.

(6) Blood Condition Analysis Step VI

The blood condition analysis step VI includes analyzing the condition of the blood sample on the basis of the electrical characteristic of the blood sample obtained by mixing by the mixing unit 13. The blood condition analysis step VI is not indispensable in the electrical characteristic measurement method according to the present technology. Alternatively, another device or method may be used to analyze the blood condition on the basis of the measurement result obtained by the electrical characteristic measurement method according to the present technology. The details of the analysis method performed in the blood condition analysis step VI are the same as those of the analysis method performed by the blood condition analysis unit 16 of the electrical characteristic measurement device 1 described above. Therefore, the description thereof is omitted here.

(7) Correction Step VII

The correction step VII includes correcting the measurement result obtained in the blood sample measurement step V. The correction step VII is not indispensable in the electrical characteristic measurement method according to the present technology. Alternatively, an external device or method may also be used to correct the measurement result obtained in the blood sample measurement step V. The details of the correction method performed in the correction step VII are the same as those of the correction method performed by the correction unit 17 of the electrical characteristic measurement device 1 described above. Therefore, the description thereof is omitted here.

(8) Storage Step VIII

The storage step VIII includes storing the measurement result obtained in the blood sample measurement step V, each analysis result obtained in the blood condition analysis step VI, the measurement result obtained in the blood sample measurement step V, and other information. The storage step VIII is not indispensable in the electrical characteristic measurement method according to the present technology. Alternatively, each result may also be output each time without being stored. The details of the storage method performed in the storage step VIII are the same as those of the storage method performed by the storage unit 18 of the electrical characteristic measurement device 1 described above. Therefore, the description thereof is omitted here.

4. Electrical Characteristic Measurement Program

The electrical characteristic measurement program according to the present technology is a program for use in measuring an electrical characteristic of a blood sample and is configured to implement a mixing function for mixing a blood cell component and a plasma component on the basis of the composition ratio between the blood cell component and the plasma component in a blood sample and a blood sample measurement function for measuring an electrical characteristic of the blood sample obtained by mixing by the mixing function.

In addition, if necessary, the electrical characteristic measurement program according to the present technology may also cause a computer to execute, for example, the separation function, the plasma examination step II, the blood component ratio measurement step IV, the blood sample measurement step V, the blood condition analysis function, the correction function, and the storage function.

In other words, the electrical characteristic measurement program according to the present technology is a program for causing a computer to execute the electrical characteristic measurement method according to the present technology described above. Therefore, the details of each function are the same as those of each step of the electrical characteristic measurement method described above, and, therefore, the description thereof is omitted here.

Note that the present technology may also have the following features.

(1)
An electrical characteristic measurement device for measuring an electrical characteristic of a blood sample, the device including:
a mixing unit configured to mix a blood cell component and a plasma component on the basis of the composition ratio between the blood cell component and the plasma component in the blood sample; and
a blood sample measurement unit configured to measure an electrical characteristic of a blood sample obtained by mixing by the mixing unit.

(2)
The electrical characteristic measurement device according to item (1), further including a blood component ratio measurement unit configured to measure the composition ratio between the blood cell component and the plasma component in the blood sample.

(3)
The electrical characteristic measurement device according to item (2), in which the blood component ratio measurement unit includes an optical detector configured to detect the boundary surface between the blood cell component and the plasma component.

(4)
The electrical characteristic measurement device according to item (2), in which the blood component ratio measurement unit includes an electrical detector configured to detect the boundary surface between the blood cell component and the plasma component.

(5)
The electrical characteristic measurement device according to any one of items (1) to (4), in which the blood sample measurement unit is configured to measure the permittivity of the blood sample.

(6)
The electrical characteristic measurement device according to any one of items (1) to (5), further including a blood condition analysis unit configured to analyze the condition of the blood sample on the basis of an electrical characteristic of the blood sample obtained by mixing by the mixing unit.

(7)
The electrical characteristic measurement device according to any one of items (1) to (6), further including a correction unit configured to correct the result of measurement of an electrical characteristic of the blood sample in accordance with the composition ratio of the plasma component.

(8)
The electrical characteristic measurement device according to any one of items (1) to (7), further including a plasma examination unit configured to examine the plasma component.

(9)
The electrical characteristic measurement device according to any one of items (1) to (8), further including a separation unit configured to separate the plasma component and the blood cell component.

(10)
An electrical characteristic measurement method for measuring an electrical characteristic of a blood sample, the method including:
a mixing step including mixing a blood cell component and a plasma component on the basis of the composition ratio between the blood cell component and the plasma component in a blood sample; and
a blood sample measurement step including measuring an electrical characteristic of a blood sample obtained by mixing by the mixing step.

(11)
A blood condition analysis system for analyzing the condition of a blood sample, the system including:
an electrical characteristic measurement device including a mixing unit configured to mix a blood cell component and a plasma component on the basis of the composition ratio between the blood cell component and the plasma component in a blood sample and a blood sample measurement unit configured to measure an electrical characteristic of a blood sample obtained by mixing by the mixing unit; and
a blood condition analysis device including a blood condition analysis unit configured to analyze the condition of the blood sample on the basis of the electrical characteristic of the blood sample obtained by mixing by the mixing unit.

(12)
The blood condition analysis system according to item (11), further including a server configured to store the result of measurement by the electrical characteristic measurement device and/or the result of analysis by the blood condition analysis device.

(13)
An electrical characteristic measurement program for use in measuring an electrical characteristic of a blood sample, the program being configured to implement a mixing function for mixing a blood cell component and a plasma component on the basis of the composition ratio between the blood cell component and the plasma component in a blood sample and a blood sample measurement function for measuring an electrical characteristic of the blood sample obtained by mixing by the mixing function.

REFERENCE SIGNS LIST

1 Electrical characteristic measurement device
11 Separation unit
12 Plasma examination unit
13 Mixing unit
14 Blood component ratio measurement unit
15 Blood sample measurement unit
16 Blood condition analysis unit
17 Correction unit
18 Storage unit
10 Blood condition analysis system
101 Blood condition analysis device
102 Server
103 Display unit
104 User interface
141 Optical detector
142 Light application unit
143 Light detection unit
144 Electrical detector
I Separation step
II Plasma examination step
III Mixing step
IV Blood component ratio measurement step
V Blood sample measurement step
VI Blood condition analysis step
VII Correction step
VIII Storage step

The invention claimed is:

1. An electrical characteristic measurement device, comprising:
a plasma examination unit configured to examine a plasma component of a blood sample;
a blood component ratio measurement unit configured to:
measure a composition ratio between a blood cell component of the blood sample and the plasma component of the blood sample; and
determine a decrease in an amount of the plasma component based on the measured composition ratio;
a mixing unit configured to:
adjust the composition ratio between the blood cell component and the plasma component based on the decrease in the amount of the plasma component, and
mix the blood cell component and the plasma component to obtain a mixed blood sample; and
a blood sample measurement unit configured to measure an electrical characteristic of the mixed blood sample.

2. The electrical characteristic measurement device according to claim 1, wherein the blood component ratio measurement unit comprises an optical detector configured to detect a boundary surface between the blood cell component and the plasma component.

3. The electrical characteristic measurement device according to claim 1, wherein the blood component ratio measurement unit comprises an electrical detector configured to detect a boundary surface between the blood cell component and the plasma component.

4. The electrical characteristic measurement device according to claim 1, wherein the electrical characteristic of the mixed blood sample includes a permittivity of the mixed blood sample.

5. The electrical characteristic measurement device according to claim 1, further comprising a blood condition analysis unit configured to analyze a condition of the mixed blood sample based on the measured electrical characteristic of the mixed blood sample.

6. The electrical characteristic measurement device according to claim 1, further comprising a correction unit configured to correct a result of measurement of the electrical characteristic of the mixed blood sample based on the composition ratio between the blood cell component and the plasma component.

7. The electrical characteristic measurement device according to claim 1, further comprising a separation unit configured to separate the blood sample into the plasma component and the blood cell component.

8. An electrical characteristic measurement method, comprising:
examining a plasma component of a blood sample;
measuring a composition ratio between a blood cell component of the blood sample and the plasma component of the blood sample;
determining a decrease in an amount of the plasma component based on the measured composition ratio;
adjusting the composition ratio between the blood cell component and the plasma component based on the decrease in the amount of the plasma component, and mixing the blood cell component and the plasma component to obtain a mixed blood sample; and
measuring an electrical characteristic of the mixed blood sample.

9. A blood condition analysis system, comprising:
an electrical characteristic measurement device comprising:
a plasma examination unit configured to examine a plasma component of a blood sample;
a blood component ratio measurement unit configured to:
measure a composition ratio between a blood cell component of the blood sample and the plasma component of the blood sample; and
determine a decrease in an amount of the plasma component based on the measured composition ratio;
a mixing unit configured to:
adjust the composition ratio between the blood cell component and the plasma component based on the decrease in the amount of the plasma component, and
mix the blood cell component and the plasma component to obtain a mixed blood sample; and
a blood sample measurement unit configured to measure an electrical characteristic of the mixed blood sample; and
a blood condition analysis device comprising a blood condition analysis unit configured to analyze a condition of the mixed blood sample based on the measured electrical characteristic of the mixed blood sample.

10. The blood condition analysis system according to claim 9, further comprising a server configured to store at least one of a result of measurement obtained from the electrical characteristic measurement device or a result of analysis obtained from the blood condition analysis device.

11. A non-transitory computer-readable medium having stored thereon computer-readable instructions, which when executed by a computer, cause the computer to execute operations for measuring an electrical characteristic of a blood sample, the operations comprising:
- examining a plasma component of the blood sample;
- measuring a composition ratio between a blood cell component of the blood sample and the plasma component of the blood sample;
- determining a decrease in an amount of the plasma component based on the measured composition ratio;
- adjusting the composition ratio between the blood cell component and the plasma component based on the decrease in the amount of the plasma component, and mixing the blood cell component and the plasma component to obtain a mixed blood sample; and
- measuring the electrical characteristic of the mixed blood sample.

\* \* \* \* \*